United States Patent [19]  [11] Patent Number: 4,554,822
Eisenhauer et al.  [45] Date of Patent: Nov. 26, 1985

[54] PLUGGING FACTOR MONITOR UNIT

[75] Inventors: Roy J. Eisenhauer, Lakewood; Cary A. Loeser, Evergreen, both of Colo.; Charles G. Goodner, Jr., Yuma, Ariz.

[73] Assignee: The United States of America as represented by the Secretary of the Interior, Washington, D.C.

[21] Appl. No.: 502,034

[22] Filed: Jun. 7, 1983

[51] Int. Cl.$^4$ ............................................. G01N 15/00
[52] U.S. Cl. ........................................ 73/61 R; 73/53
[58] Field of Search ................. 73/61 R, 38, 53, 61.4, 73/64.3

[56] References Cited

U.S. PATENT DOCUMENTS 3,308,649 3/1967 Colechia .............................. 73/61 R
3,686,925 8/1972 Fleisch et al. ....................... 73/61 R
3,893,333 7/1975 Sunahara et al. ................... 73/61 R
4,229,971 10/1980 Ririe, Jr. ............................. 73/61 R Primary Examiner—Stewart J. Levy
Assistant Examiner—Joseph W. Roskos
Attorney, Agent, or Firm—Thomas Zack

[57] ABSTRACT

A plugging factor (PF) monitor unit is provided for measuring the quality of the prefiltered feed water supplied to the membrane of a membrane-type desalting plant in accordance with a standard PF test. Samples from sample point selector booster pump unit are selectively diverted to the monitor after being pumped to the required pressure level. A filter membrane holder assembly receives test membranes from a continuous supply and clamps a test membrane in place so that the sample water flows therethrough to a filtrate tank used in measuring out a predetermined standard volume. A control unit controls supplying of the sample water to the monitor unit as well as discharging of the filtrate from the tank such that the time taken to measure out the standard volume is determined at two spaced time periods in accordance with the standard test. Provision is made for preventing breakage of the membrane during testing.

18 Claims, 2 Drawing Figures

PLUGGING FACTOR MONITOR UNIT

FIELD OF THE INVENTION

This invention relates to membrane-type desalting plants and, more particularly, to an automated plugging factor monitor for measuring the quality of the prefiltered feed water supplied to the membrane of said plants.

BACKGROUND OF THE INVENTION

Desalting plants which use membranes in the desalting process must monitor the membrane performance to ensure stable operation. The quality of prefiltered water delivered to the membranes of such plants largely determines the membrane performance and longevity. Feed water quality can be monitored using a "plugging factor" (PF) method which indicates the quantity of particulate matter present in the feed water to the desalting membranes. A manual test was developed in the early 1970s and has been generally accepted through the industry as a criterion for determining the fouling tendency of membrane feed water. In this regard, membrane manufacturers use this PF as an indication of desalting unit feed water quality.

The plugging factor test itself is a measurement of the percent decrease of flow rate through a 0.45 mm filter membrane with a constant pressure differential of 207 kPa (gauge) after 15 minutes. This can be represented by the formula $$\% \; PF = \left(1 - \frac{t_2}{t_1}\right) \times 100,$$

where the quantity $t_1$ is the time period of the initial measurement and $t_2$ is the time period of the measurement performed 15 minutes later. It is theorized that the decreased flow is due to particles plugging some of the pores of the filter membrane and accordingly, the resultant percentage of flow reduction is related to the percent of plugged pores. If the total number of pores in a new filter membrane and the total volume of fluid flow during the test are known, the number of plugging particles per unit volume can be calculated.

A manual system such as referred to above has obvious shortcomings particularly with respect to the considerable amount of operator time required, and attempts have been made to develop an automatic continuous plugging factor monitor. One such continuous plug factor monitor which has been evaluated employed a filter holder assembly comprising a pressure actuated upper filter head movable to an operative position wherein a membrane filter, supplied from a membrane tape feed roll by action of a puller motor, is captured between the upper filter head and a lower filter head or base. The sample water under test flowed through the membrane held by the filter holder assembly to a filtrate tank including level probes which extended into the tank and which were used in determining the time required for a standard predetermined volume (131 ml) to be measured out. Two such time period determinations were made, corresponding to the periods $t_1$ and $t_2$ of the PF formula discussed above, and a programmer was used to control sequencing of the operations of the off-on valves in the system, the puller motor for the membrane tape and the upper filter head actuator. Cycle and interval timers provided inputs to the programmer and an event recorder used in displaying the values $t_1$ and $t_2$ was connected to the output thereof.

Continuous plugging factor monitors that have been developed to date possess several disadvantages which have limited their usefulness. These disadvantages include poor precision, particularly for plugging factors lower than 50%; poor system reliability (caused principally by breakage of filter tape); and limitations on calculation and recording of PF results.

SUMMARY OF THE INVENTION

In accordance with the invention, a continuous automatic plugging factor testing and monitoring system is provided which overcomes the disadvantages of the prior art discussed above. The testing and monitoring system of the invention, includes, in a manner similar to or in common with the prior art system described above, the following basic components: regulating and monitoring means for receiving a water sample and for regulating the pressure of a sample to be tested; filter holder means, broadly similar to that described above, for receiving a test sample; and filter membrane supply means, also broadly similar to that described above, for automatically supplying a filter membrane to the filter holder means, the filter holder means including a base member, and a movable member (upper filter head) movable between a first, inoperative position and a second, operative position in engagement with the base member wherein the filter membrane is held in a test position between the movable and base members. The filter holder means further includes means defining a flow path through the movable member, a filter membrane held by the filter holder means in the test position thereof and the base member, so that a test sample received by the filter holder means flows through the filter membrane. The system also includes a collector tank means, basically similar to that described previously and connected to the outlet of the flow path of said filter holder means, for collecting the test sample flowing through the membrane under test and for measuring the filling time required for the test sample flow to reach a predetermined volume (131 ml in the standard PF test). A discharge valve means controls discharge of the contents of the collector tank means and an automatic control means provides monitoring the operation of the collector tank means and controls the operation of the discharge valve means such that (1) the discharge valve means is closed until a first said predetermined (131 mL) volume is measured out by the collector tank means and the filling time required to produce the first volume is measured, (2) the discharge valve means is then opened so that the contents of the collector tank means are discharged, and (3) after a predetermined time period set by said automatic control means (15 minutes in the standard PF test), the discharge valve means is closed so that a second said predetermined (131 mL) volume is measured out by the collector tank means and the filling time required to produce the second volume is measured.

In accordance with an important feature of the invention, the filter membrane supply means comprises means for providing raising of the filter membrane a predetermined distance off of the base member of the filter holder when the movable member is moved to the first, inoperative position thereof. This approach serves in eliminating breakage of the fragile filter membrane tape and, in particular, eliminates the problem associated with the prior art device mentioned above wherein the tape tended to adhere to the lower filter head and thus when the tape was advanced, the drag of the tape on the lower filter head frequently resulted in breakage of the tape.

In accordance with a further important feature of the invention, a valve means is located upstream of the filter holder means which is operable responsive to the automatic control means to open at the end of each measuring cycle so as to lower the pressure at the movable member of the filter holder means prior to movement of that movable member to the inoperative position thereof. This prevents water in the movable member from flooding and weakening the filter membrane.

According to yet a further important aspect of the invention, the water sample receiving means comprises a plurality of three-way selector valves connected to a like plurality of sample sources. Each selector valve provides flow of the test water from the corresponding sample source to drain until that valve is selected. This prevents contamination of a given water sample by a previous sample. Preferably, the system further comprises a further three-way valve located downstream of said plurality of three-way valves for selectively diverting the sample water from the selected valve to the filter holder means. Actuation and de-actuation of the further three-way valve is controlled by the automatic control means. Advantageously, each of the plurality of three-way valves comprises a three-way air-operated diverter valve and the system further comprises a like plurality of solenoid-controlled air valves, responsive to the automatic control means, for respectively controlling actuation of the air-operated diverter valves, the air valves being connected to a common air manifold and the diverter valves being connected to a common water manifold. A two stage turbine impeller type centrifugal pump is preferably used to raise the pressure of the sample water to the aforesaid predetermined pressure (207 kPa).

The automatic control means comprises an electronic control unit which provides automatical operation of the mechanical test unit described above through a complete test cycle and then calculates, displays, and prints out the PF and other data and thereafter, as desired, inputs the data to a computer or data acquisition system.

Other features and advantages of the present invention will be set forth in, or apparent from, the detailed description of the preferred embodiments of the invention found hereinbelow.

DESCRIPTION OF THE PREFERRED EMBODIMENTS

Figure 1:
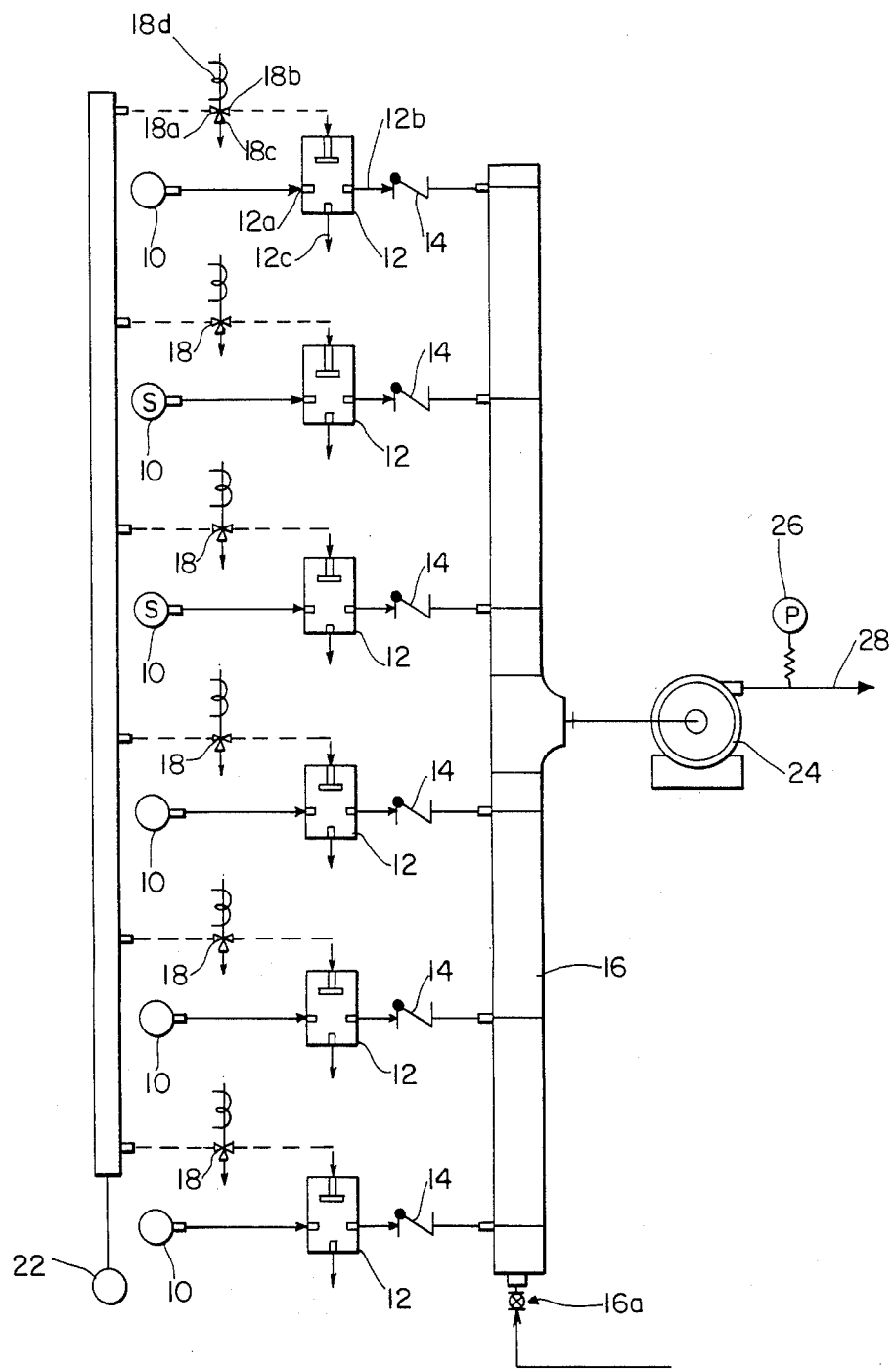
FIG. 1 is a schematic diagram of the sample point selector booster pump unit of the invention.

Referring to FIG. 1, a schematic diagram of a sample point selector booster pump (SPSBP) unit is shown. The system includes a plurality of water sample sources, indicated at 10, and in the specific embodiment under consideration, six water sample sources are provided so that plugging factor tests can be run on any one of six samples. The sample water sources 10 are individually connected through respective three-way, compressed air-operated diverter valves 12 and respective check valves 14 to a common water manifold 16.

The operation of each diverter valve 12 is controlled by a corresponding three-way solenoid operated air valve 18. Air valves 18 are connected to a common air manifold which is, in turn, connected to a padding air source 22. The solenoid operated air valves 18 each include an input port 18a, an outlet port 18b and an air vent or port 18c and depending on whether or not an associated solenoid, denoted 18d, is energized, air from the inlet port will be either supplied to the corresponding diverter valve 12 through port 18b to energizing valve 12 or vented through port 18c to deenergizing valve 12. Energization of the solenoids is controlled from a central console described below.

Similarly, diverter valves 12 each include an input port 12a, an outlet port 12b and a water drain 12c and depending on whether or not air is supplied from the corresponding air valve 18, the sample water from the respective source 10 is either supplied to manifold 16 through port 12b or diverted through water drain 12c.

The outlet of water manifold 16 is pumped by a two stage turbine impeller type centrifugal pump 24 (providing, in a specific example, (100 mL/min at a nominal 214 kPa) to create an inlet water sample stream for the plugging factor monitor described in connection with FIG. 2. To start up the sample point selector booster pump unit decavitation water is supplied to water manifold 16 through an inlet valve 16a. A pressure gauge 26 is used in maintaining a suitable pressure for the monitor unit (about 207 kPa for the specific standard PF test referred to above). The pump 24 provides an increase in pressure from the filter plant pressure to the monitor unit pressure referred to above. The inlet line to the monitor unit is indicated at 28.

Figure 2:
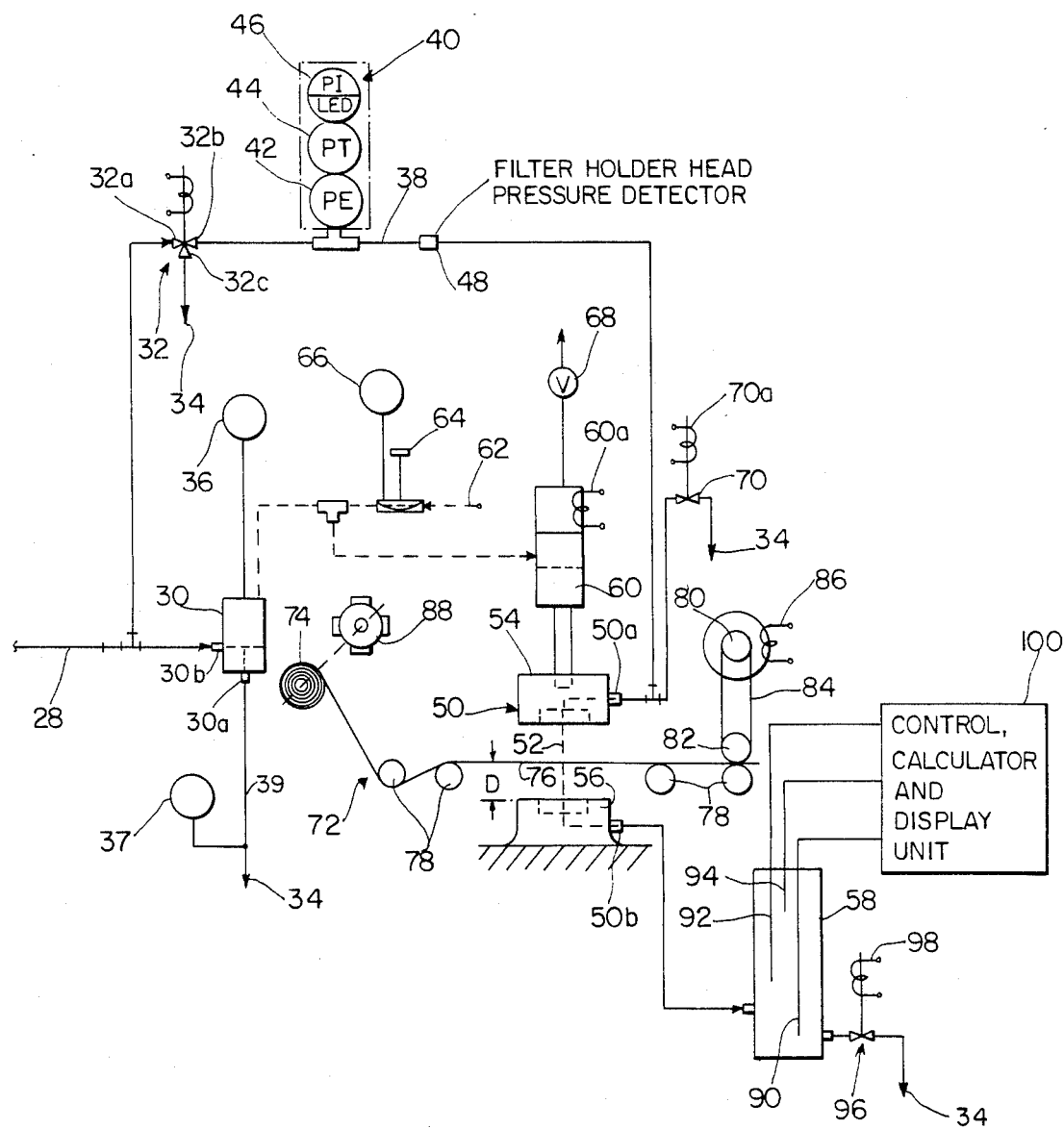
FIG. 2 is a schematic diagram of the plugging factor monitor and tester unit of the invention.

Referring to FIG. 2, sample water stream in the inlet line 28 from the SPSBP unit described above is connected to a back pressure diverter 30 through inlet port 30b as well as to a main flow three-way solenoid-operated valve 32. Diverter valve 30 is air pressure controlled and acts to hold the sample stream pressure constant through relieving overpressure by diverting part of the water flow to a drain 34. A first pressure gauge 36 is connected to diverter 30 to monitor the pressure therein while a further pressure gauge 37 is connected to the bypass flow line 39 connected between the drain port 30a of diverter 30, and drain 34.

Three-way solenoid-operated valve 32 is similar to the valves described above and includes inlet port 32a, outlet port 32b and drain port 32c. When de-energized valve 32 provides for diverting of all of the flow through drain port 32c to the drain 34 (the numeral 34 being used to represent a common drain through the system).

Outlet drain port 32b is connected through a "tester ON" flow line 38 to a pressure gauge arrangement 40 which includes a pressure sensor element 42, a pressure transmitter 44 and a pressure gauge 46. Flow line 38 is connected through a filter pressure head pressure detector 48 to an inlet port 50a of a filter holder assembly 50. The filter holder assembly 50 supports a section of filter paper therein as described below and provides a path, indicated schematically in dotted lines at 52, through which the test water flows. Filter holder 50 includes a movable, upper head portion 54 and fixed, lower base portion 56, head portion 54 being shown in the raised position thereof in FIG. 2. It will be understood that the flow path through filter holder assembly 50 is interrupted when portion 54 is raised and that the sample flow would be cut off under these circumstances. An outlet port 50b in base portion 56 of filter holder assembly 50 is connected to a collector or measuring tank 58 described below.

Movement of movable portion 54 of filter holder assembly 50 is controlled by an electrical-air powered operator or actuator 60. Air for operator 60, and for diverter valve 30 described above, is supplied from a compressed air supply line 62 through an air regulator valve 64. A further pressure gauge 66 is used in maintaining the pressure at the predetermined valve selected (as noted above, this pressure is 207 kPa in the specific example being considered). An air release valve 68 is connected to operator 60 while a solenoid control winding for operator 60 is indicated at 60a. Energization of solenoid 60a is automatically controlled from the central console as described below. A solenoid-operated two-way pressure relief valve 70 is associated with the connection to filter holder inlet port 50a. Energization of solenoid 70a of valve 70 is also remotely controlled to provide discharge of line 38 into the drain 34 to relieve the pressure in line 38.

The filter paper or tape (membrane) for filter holder assembly 50 is supplied by a paper feed system generally denoted 72 and including a supply roll 74 from which the filter paper, generally denoted 76, is fed to filter holder 50 through an arrangement of support and idler rollers 78 under the control of a paper feed drive motor 80. Motor 80 is connected to a drive roller 82 through a drive belt 84. Energization of the motor windings 86 of motor 80 is controlled from the central control console. A paper fault detector 88 comprises an electric eye that senses the rotation of the hub of the filter tape feed spool or roller 74.

The collector tank 58, which, as referred to above, receives the filtered water from outlet port 50b, is used in metering out a predetermined volume of the water in a conventional manner. As illustrated, the collector tank 58 includes a ground electrode probe 90, a "start" electrode probe 92 and a "stop" electrode probe 94, which extend into tank 58 to varying depths. The collector tank is conventional in construction and operation and it will be understood that the system will be initially actuated or started in operation when the water level in tank 58 reaches the level of the "start" electrode probe 92 and will be de-energized or stopped when the water level reaches the level of the "stop" electrode probe 94. A two-way solenoid-operated valve 96 is used in discharging the water from tank 58 to the drain 34 before the test begins and after testing has been completed, in response to de-energization of solenoid control winding 98. The electrode probes 90, 92 and 94 are connected to a control unit 100 whose function is described below.

Considering the overall operation of the system, and beginning with the SPSBP unit of FIG. 1, this unit is used to automatically select water samples from any one of the six different sources 10. When one of the three-way diverter valves 12 is actuated, water is diverted to the water manifold 16 and from thence to the centrifugal pump 24. Pump 24 increases the pressure of the water from the filter plant pressure to the PF monitor tester pressure (207 kPa in the specific example being considered, corresponding to the standard PF test pressure). The SPSBP unit then delivers sample water flow, at the correct pressure, to the tester unit of FIG. 2.

Continuing on with a consideration of the system operation, the PF tester monitor unit of FIG. 2 receives the sample flow at the pressure determined by pump 24. This pressure is held constant by back pressure diverter 30 which, as explained above, relieves any over pressure by diverting part of the water flow to drain 34.

During "test OFF" conditions, i.e., prior to the actual test operation, main flow valve 32 and pressure relief valve 70 are de-energized, and all of the flow in line 38 is diverted to drain 34. During the "test ON" condition, valves 32 and 70 are energized and the sample water passes through line 38 to filter holder 50.

At the beginning of each test, the paper drive motor 80 is energized through winding 86 and acts to advance the filter paper or membrane a predetermined distance through the open space between filter holder head 54 and base 56. In the specific example under consideration, this distance is 40 mm and the filter area is 345 cm$^2$, while the filter membrane is of a pore size of 0.45 $\mu$m in accordance with the standard PF test. The electric-and-air operated piston or operator 60 is then energized to compress the filter paper 76 between the filter holder head 54 and base 56. When the three-way solenoid way 32 is energized (the "test ON" condition), the flow to the drain 34 is shut off and the flow is instead diverted to the filter holder assembly. Sample water flows through the filter paper 76 held in holder 50 and enters the measuring collector tank 58. At this time, the water flows through the normally opened, solenoid-controlled test drain control valve 96 to the drain 34.

The actual test begins when the test drain control valve 96 is energized, thereby closing the drain and permitting the tank 58 to begin filling. The testing time period begins when the water level reaches start electrode 92 and ends when the water level reaches the stop electrode 94. This is detected by control unit 100 which then de-energizes winding 98 of drain control valve 96 so that valve 96 opens. The spacing of lower and upper electrodes 92 and 94 is such that a predetermined volume of water (131 ml in a specific example) is measured between closing and opening of valve 96. The time period required is $t_1$ of the plugging factor formula set forth above.

When the valve 96 opens, tank 58 is drained and the sample stream of water is allowed to flow for a predetermined time period, specifically 15 minutes, into the drain 34.

After 15 minutes, the valve 96 is closed again, and the time it takes for a second volume to be filled is measured using start and stop electrode probes 92 and 94 as described above. This time period is $t_2$. With this data, the percentage plugging factor is calculated using the formula $$\% PF = \left(1 - \frac{t_2}{t_1}\right) \times 100.$$

The electronic control unit 100 is the key element of the central console referred to above, and it will be seen that electronic control unit 100, by controlling energization of the various solenoid operated valves and the other electrically controlled devices (e.g., operator 60 and motor 80), can automatically control the mechanical test unit through a complete test cycle. Further, the control unit 100 is also equipped to calculate, display, and print out the PF and other test data, and to input the data to a computer or other data acquisition system. No other known prior art systems, similar to ours, is capable of performing all these desired functions with the same complex outputs.

As mentioned above, the tester unit of the invention possesses a number of important features. For example, during each cycle a sample uncontaminated by the preceding sample is tested. In this regard, contamination of the water sample under test by a previous water sample is prevented by using three-way valves 12 for each sample point selection so as to permit water to continuously flow to drain from all six sample sources 10 until a specific selector valve is actuated. Further, three-way valve 32, located downstream of pump 24 and upstream of the monitor tester unit, permits the water discharging from the pump 24 to continuously bypass to the drain 34 until diverted to filter holder assembly 50. In addition, the pressure of the test sample of water is continually and precisely maintained at the setpoint of 207 kPa. In addition, automatic and precise advancement of the membrane filter tape 76 is provided for each test cycle.

Other important advantages involve the manner in which breakage of the fragile membrane filter tape is prevented, such breakage being a serious problem with prior art automated systems. First, water in the upper filter head portion 54 is prevented from flooding and weakening the tape 76 by means of normally open pressure relief valve 70 which is located upstream thereof and deenergized to open at the end of each cycle, thereby dropping the pressure in the upper filter head 54 before the latter lifts off of the membrane tape 76. Further, the membrane tape is kept under tension by the arrangement of feed spool 74, stationary spools and idler rollers 78, and puller roller 82, and the construction is such that when the upper filter head portion 54 lifts away from the lower filter head portion 56, the membrane tape 76 will raise a predetermined distance "D" (1/32 inch) above lower filter head portion 56. In prior art arrangements, the membrane tape tended to adhere to the lower filter head and when the tape was advanced, the drag of the tape on the lower filter head frequently resulted in breakage of the tape. The membrane filter tape advance sequence is monitored by paper fault detector 88 which as noted, senses the turning of the hub of the feed spool 74.

The member feed spool 74 is designed to take a full roll of the tape as provided by the membrane tape manufacturer.

Further, all surfaces of the mechanical units wetted during the system operation are constructed of materials that are resistant to salt water corrosion.

Although the invention has been described in detail with respect to an exemplary embodiment thereof, it will be understood by those of ordinary skill in the art that variations and modifications may be effected in this embodiment within the scope and spirit of the invention.

We claim:

1. A continuous automatic plugging factor testing and monitoring system, said system comprising:
   means for receiving water samples and for raising the pressure of a sample to be tested to a predetermined test pressure;
   means for continuously monitoring the pressure of the test sample;
   filter holder means for receiving a test sample at said predetermined test pressure;
   means for automatically supplying a filter membrane to said filter holder means, said filter holder means including a base member, and a movable member between a first, inoperative position and a second, operative position in engagement with said base member wherein said filter membrane is held in a test position between said movable member and said base member, said filter holder means further including means defining a flow path through said movable member, a filter membrane in the test position thereof and the base member;
   collector tank means, connected to the outlet of the flow path of said filter holder means, for collecting the test sample flowing through the membrane under test and for measuring the filling time required for the test sample flow to reach a predetermined volume;
   discharge valve means for controlling discharge of the contents of the collector tank means; and
   automatic control means for monitoring the operation of said collector tank means and controlling the operation of said discharge valve means such that the discharge valve means is closed until a first said predetermined volume is measured out by said collector tank means and the filling time required to produce the first volume is measured, the discharge valve means is then opened so that the contents of the collector tank means are discharged through said discharge valve means, and after a predetermined time period set by said said automatic control means, the discharge valve means is closed so that a second said predetermined volume is measured out by said collector tank means and the filling time required to produce the second volume is measured,
   said filter membrane supplying means comprising means for providing raising of the filter membrane a predetermined distance from the base member of the filter holder when the movable member is moved to the first, inoperative position thereof.

2. A system as claimed in claim 1 wherein said water sample receiving means comprises a plurality of three-way selector valves connected to a like plurality of sample sources, each said selector valve providing flow of the test water from the corresponding sample source to drain until that valve is selected.

3. A system as claimed in claim 2 wherein said system further comprises a further three-way valve located downstream of said plurality of three-way valves for selectively diverting the sample water from the selected valve to the filter holder means, actuation and de-actuation of said further three-way valve being controlled by said automatic control means.

4. A system as claimed in claim 2 wherein said plurality of three-way valves each comprises a three-way air-operated diverter valve and wherein said system further comprises a like plurality of solenoid-controlled air valves, responsive to said automatic control means, for respectively controlling actuation of said diverter valves, said air valves being connected to a common air manifold and said diverter valves being connected to a common water manifold.

5. A system as claimed in claim 1 wherein said sample receiving means further comprises a centrifugal pump for raising the pressure of the selected sample to said predetermined pressure.

6. A system as claimed in claim 1 wherein said system further comprises valve means located upstream of said filter holder means and operable responsive to said automatic control means to open at the end of each measuring cycle so as to lower the pressure at the movable member of said filter holder means prior to movement of the movable member to the first, inoperative position thereof.

7. A system as claimed in claim 1 wherein said filter membrane supplying means comprises a feed spool, a motor for pulling the membrane from the feed spool and means for monitoring the rotation of said feed spool.

8. A system as claimed in claim 7 wherein said water sample receiving means comprising a plurality of three-way selector valves connected to a like plurality of sample sources, each said selector valve providing flow of the test water from the corresponding sample source to drain until that valve is selected.

9. A system as claimed in claim 8 wherein said system further comprises a further three-way valve located downstream of said plurality of three-way valves for selectively diverting the sample water from the selected valve to the filter holder means, actuation and de-actuation of said further three-way valve being controlled by said automatic control means.

10. A system as claimed in claim 8 wherein said plurality of three-way valves each comprises a three-way air-operated diverter valve and wherein said system further comprises a like plurality of solenoid-controlled air valves, responsive to said automatic control means, for respectively controlling actuation of said diverter valves, said air valves being connected to a common air manifold and said diverter valves being connected to a common water manifold.

11. A system as claimed in claim 8 wherein said sample receiving means further comprises a centrifugal pump for raising the pressure of the selected sample to said predetermined pressure.

12. A system as claimed in claim 8 wherein said filter membrane supply means comprises means for providing raising of said movable member a predetermined distance from said base member when the movable member is moved to the first, inoperative position thereof.

13. A continuous automatic plugging factor testing and monitoring system, said system comprising:
means for receiving water samples and for raising the pressure of a sample to be tested to a predetermined test pressure;
means for continuously monitoring the pressure of the test sample;
filter holder means for receiving a test sample at said predetermined test pressure;
means for automatically supplying a filter membrane to said filter holder means, said filter holder means including a base member, and a movable member movable between a first, inoperative position and a second, operative position in engagement with said base member wherein said filter membrane is held in a test position between said movable member and said base member, said filter holder means further including means defining a flow path through said movable member, a filter membrane in the test position thereof and the base member;
collector tank means, connected to the outlet of the flow path of said filter holder means, for collecting the test sample flowing through the membrane under test and for measuring the filling time required for the test sample flow to reach a predetermined volume;
discharge valve means for controlling discharge of the contents of the collector tank means; and
automatic control means for monitoring the operation of said collector tank means and controlling the operation of said discharge valve means such that the discharge valve means is closed until a first said predetermined volume is measured out by said collector tank means and the filling time required to produce the first volume is measured, the discharge valve means is then opened so that the contents of the collector tank means are then discharged through said discharge valve means, and after a predetermined time period set by said automatic control means, the discharge valve means is closed so that a second said predetermined volume is measured out by said collector tank means and the filing time required to produce the second volume is measured;
said system further comprising valve means located upstream of said filter holder means and operable responsive to said automatic control means to open at the end of each measuring cycle so as to lower the pressure at the movable member of said filter holder means prior to movement of the movable member to the first, inoperative position thereof.

14. A continuous automatic plugging factor testing and monitoring system, said system comprising:
means for receiving water samples and for raising the pressure of a sample to be tested to a predetermined test pressure;
means for continuously monitoring the pressure of the test sample;
filter holder means for receiving a test sample at said predetermined test pressure;
means for automatically supplying a filter membrane to said filter holder means, said filter holder means including a base member, and a movable member movable between a first, inoperative position and a second, operative position in engagement with said base member wherein said filter membrane is held in a test position between said movable member and said base member, said filter holder means further including means defining a flow path through said movable member, a filter membrane in the test position thereof and the base member;
collector tank means, connected to the outlet of the flow path of said filter holder means, for collecting the test sample flowing through the membrane under test and for measuring the filling time required for the test sample flow to reach a predetermined volume;
discharge valve means for controlling discharge of the contents of the collector tank means;
automatic control means for monitoring the operation of said collector tank means and controlling the operation of said discharge valve means such that the discharge valve means is closed until a first predetermined volume is measured out by said collector tank means and the filling time required to produce the first volume is measured, the discharge valve means is then opened so that the contents of the collector tank means are discharged through said discharge valve means, and after a predetermined time period set by said automatic control means, the discarge valve means is closed so that a second said predetermined volume is measured out by said collector tank means and the filling time required to produce the second volume is measured;

said water sample receiving means comprising a plurality of three-way selector valves connected to a like plurality of sample sources, and each said selector valve provides flow of the test water from the corresponding sample source to drain until that valve is selected, said system further comprising a further three-way valve located downstream of said plurality of three-way valves for, when deactuated, diverting the sample water from the selected valve to the filter holder means, actuation and de-actuation of said further three-way valve being controlled by said automatic control means.

15. A system as claimed in claim 14 wherein said system further comprises a further three-way valve located downstream of said plurality of three-way valves for, when de-activated, diverting the sample water from the selected valve to the filter holder means, actuation and de-actuation of said further three-way valve being controlled by said automatic control means.

16. A system as claimed in claim 15 wherein said plurality of three-way valves each comprises a three-way diverter valve and wherein said system further comprises a like plurality of solenoid-controlled air valves, responsive to said automatic control means, for respectively controlling actuation of said diverter valves, said air valves being connected to a common air manifold and said diverter valves being connected to a common water manifold.

17. A system as claimed in claim 15 wherein said sample receiving means further comprises a centrifugal pump for raising the pressure of the selected sample to said predetermined pressure.

18. A system as claimed in claim 14 wherein said filter membrane supply means comprises a feed spool for said filter membrane and said system further comprises means for sensing the rotation of said feed spool.

* * * * *